US012579767B2

(12) United States Patent
Krans et al.

(10) Patent No.: US 12,579,767 B2
(45) Date of Patent: Mar. 17, 2026

(54) AUGMENTED-REALITY SYSTEMS AND METHODS FOR GUIDED INSTALLATION OF MEDICAL DEVICES

(71) Applicant: KONINKLIJKE PHILIPS N.V., Eindhoven (NL)

(72) Inventors: Jan Martijn Krans, Eindhoven (NL); Dietwig Jos Clement Lowet, Tongeren (BE)

(73) Assignee: Koninklijke Philips N.V., Eindhoven (NL)

( * ) Notice: Subject to any disclaimer, the term of this patent is extended or adjusted under 35 U.S.C. 154(b) by 171 days.

(21) Appl. No.: 18/623,451

(22) Filed: Apr. 1, 2024

(65) Prior Publication Data

US 2024/0338907 A1     Oct. 10, 2024

Related U.S. Application Data

(60) Provisional application No. 63/456,915, filed on Apr. 4, 2023.

(51) Int. Cl.
*G06T 19/00* (2011.01)
*A61B 5/00* (2006.01)
(Continued)

(52) U.S. Cl.
CPC ............ *G06T 19/006* (2013.01); *A61B 5/684* (2013.01); *A61B 10/00* (2013.01); *G06T 7/70* (2017.01);
(Continued)

(58) Field of Classification Search
None
See application file for complete search history.

(56) References Cited

U.S. PATENT DOCUMENTS

2014/0267408 A1     9/2014  Mullins
2017/0112439 A1     4/2017  Dubin
(Continued)

FOREIGN PATENT DOCUMENTS

CN     106374382  A     2/2017
CN     107692965  A     2/2018
(Continued)

OTHER PUBLICATIONS

Buck et al., An Augmented Reality System for Patient-Specific Guidance of Cardiac Catheter Ablation Procedures, Nov. 30, 2005, IEEE Transactions on Medical Imaging, vol. 24, No. 11, 1512-1524 (Year: 2005).*
International Search Report for PCT/EP2024/058735 filed Mar. 29, 2024.

*Primary Examiner* — Robert J Craddock

(57)     ABSTRACT

The present disclosure relates to augmented-reality systems and methods, and more specifically to systems and methods of providing automated support instructions to patients during medical device unboxing and installation via an augmented reality-enabled device. While adoption of remote patient monitoring and remote patient care (e.g., telehealth) has greatly accelerated, most medical devices are not designed for usage by laypersons. Thus, the systems and methods of the present disclosure provide easy and accessible guidance to patients now tasked with unboxing and installation complex medical devices without the support of a trained healthcare professional.

15 Claims, 6 Drawing Sheets

(51) Int. Cl.

| | | |
|---|---|---|
| *A61B 10/00* | (2006.01) | |
| *G06T 7/70* | (2017.01) | |
| *G06T 19/20* | (2011.01) | |
| *G16H 40/40* | (2018.01) | |
| *G16H 40/67* | (2018.01) | |
| *A61B 90/00* | (2016.01) | |

(52) U.S. Cl.
CPC ............. *G06T 19/20* (2013.01); *G16H 40/40* (2018.01); *G16H 40/67* (2018.01); *A61B 2010/0003* (2013.01); *A61B 2090/365* (2016.02); *A61B 2505/07* (2013.01); *G06T 2200/08* (2013.01); *G06T 2207/10016* (2013.01); *G06T 2207/30196* (2013.01); *G06T 2210/41* (2013.01); *G06T 2219/2016* (2013.01)

(56) References Cited

U.S. PATENT DOCUMENTS

| | | | |
|---|---|---|---|
| 2017/0265806 A1 | 9/2017 | Albert | |
| 2017/0366749 A1 | 12/2017 | Zolotov | |
| 2020/0005481 A1 * | 1/2020 | Mandwal | |
| 2020/0027568 A1 * | 1/2020 | Foshee, Jr. ............. | A61B 1/227 |
| 2020/0311429 A1 | 10/2020 | Chen | |
| 2021/0225497 A1 | 7/2021 | Divine | |
| 2022/0254019 A1 | 8/2022 | Connor | |

FOREIGN PATENT DOCUMENTS

| | | |
|---|---|---|
| CN | 110599603 A | 12/2019 |
| CN | 215420529 U | 1/2022 |

\* cited by examiner

200

201

PROCESSORS 202

POWER SUPPLY 210

SYSTEM BUS 208

INTERFACE BUS 206

NETWORK INTERFACE 212

I/O INTERFACE 216

MEMORY INTERFACE 218

MEMORY 204

STORAGE DEVICE 224

INSTRUCTIONS 228

DATA 226

OPERATING SYSTEM 232

220

222

214

230

211

DISPLAY 104

FIRST CAMERA 106

SECOND CAMERA 112

400

405 → RECEIVE VIDEO DATA FROM AT LEAST A FIRST CAMERA

410 → SEND AT LEAST A PORTION OF THE VIDEO DATA TO A REMOTE CONTENT SERVER

415 → RECEIVE SETUP INFORMATION ASSOCIATED WITH A MEDICAL DEVICE IDENTIFIED IN THE VIDEO DATA

420 → CREATE A FIRST COMPOSITE VISUAL FEED FROM THE SETUP INFORMATION AND THE VIDEO DATA

425 → DISPLAY THE FIRST COMPOSITE VISUAL FEED

AUGMENTED-REALITY SYSTEMS AND METHODS FOR GUIDED INSTALLATION OF MEDICAL DEVICES

CROSS-REFERENCE TO RELATED APPLICATIONS

This patent application claims the priority benefit under 35 U.S.C. § 119 (e) of U.S. Provisional Application No. 63/456,915, filed on Apr. 4, 2023, the contents of which are herein incorporated by reference.

FIELD OF THE DISCLOSURE

The present disclosure relates generally to augmented reality systems and methods, and more specifically to augmented-reality systems and methods adapted to assist patients in unpackaging and deploying medical devices in an outpatient setting.

BACKGROUND

Since the COVID-19 pandemic, adoption of remote patient monitoring (RPM) and remote patient care in general has accelerated and has become a necessary and integral part of healthcare services continuum for many different types of patients. Medical devices adapted for RPM provide care teams with the tools they need to remotely track the health of their patients at home, collaborate with the patients' doctors and help detect new medical issues or exacerbation of existing conditions before they lead to hospital readmission. However, challenges remain in successfully treating and/or managing patient outcomes through RPM programs. For example, many patients do not have the skills or basic medical expertise necessary to effectively use various medical devices in an outpatient setting. As a result, when patients do not feel confident in their ability to operate these medical devices, compliance with the RPM program drops. Further, even when unexperienced patients attempt to use an unfamiliar medical device, the patient may not know the best way to use the device. Thus, there remain significant challenges to enabling quality healthcare in remote patient settings.

SUMMARY OF THE DISCLOSURE

According to various embodiments and implementations of the present disclosure, a system for improving compliance and accuracy of usage of a medical device configured to be coupled to a subject in an outpatient setting is provided. The medical device may include at least one physiological sensor configured to measure at least one physiological parameter associated with the subject when the medical device is coupled to the subject, and the system may include: (A) an augmented reality-enabled device comprising a display, at least a first camera, and one or more processors in communication with the display and at least the first camera, wherein the one or more processors are configured to: (i) receive, via at least the first camera, video data comprising images of the medical device and/or a packaging of the medical device; (ii) communicate with a remote content server to transmit the images of the medical device and/or the packaging of the medical device and to receive setup information associated with the medical device, wherein the setup information comprises three-dimensional model data associated with the medical device and/or the packaging of the medical device; (iii) create a first composite visual feed from the three-dimensional model data and the video data received via at least the first camera; and (iv) display, via the display of the augmented reality-enabled device, the first composite visual feed.

In an aspect, the setup information further includes instructions having one or more steps for unpackaging and/or coupling the medical device to the subject.

In an aspect, the one or more processors of the augmented reality-enabled device are further configured to: create a first composite visual feed from the three-dimensional model data and the video data received via at least the first camera, wherein the first composite visual feed includes at least a portion of the instructions having one or more steps for unpackaging and/or coupling the medical device to the subject; and display, via the display of the augmented reality-enabled device, the first composite visual feed comprising at least the portion of the instructions.

In an aspect, the augmented reality-enabled device further includes at least a second camera, the first camera having a first field of view and the second camera having a second field of view that is different from the first field of view, and the one or more processors of the augmented reality-enabled device are further configured to: receive, via at least the second camera, video data including images of the medical device and at least a portion of the subject's body; communicate with the remote content server to transmit the images of the portion of the subject's body and receive body modeling data associated with the subject's body; create a second composite visual feed from the received body modeling data and the video data received via at least the second camera; and display, via the display of the augmented reality-enabled device, the second composite visual feed.

In an aspect, the one or more processors of the augmented reality-enabled device are further configured to: detect, based on the video data received from at least the first camera, completion of a predetermined action associated with the medical device and/or the packaging of the medical device; and automatically switch from receiving video data via at least the first camera to receiving video data via at least the second camera.

In an aspect, the predetermined action is indicative of the medical device leaving a first field of view of at least the first camera of the augmented reality-enable device.

In an aspect, the predetermined action is indicative of the medical device entering a second field of view of at least the second camera of the augmented reality-enabled device.

In an aspect, the one or more processors of the augmented reality-enable device are further configured to: track, using the video data received via at least the first camera, a relative position and/or orientation of the medical device and/or the packaging of the medical device; and create a first composite visual feed from the three-dimensional model data and the video data received via at least the first camera, wherein the first composite visual feed is a dynamic composite visual feed that updates a relative position and/or orientation of the three-dimensional model data based on the tracking of the relative position and/or orientation of the medical device and/or the packaging of the medical device.

In an aspect, the one or more processors of the augmented reality-enabled device are further configured to: track, using the video data received via at least the second camera, a relative position and/orientation of the subject's body; and create a second composite visual feed from the body modeling data and the video data received via at least the second camera, wherein the second composite visual feed is a dynamic composite visual feed that updates a relative position and/or orientation of the body modeling data based on the tracking of the relative position and/or orientation of the subject's body.

In an aspect, the one or more processors of the augmented reality-enabled device are further configured to: identify, based on the video data received via at least the first camera, a type of the medical device and/or a packaging status of the medical device.

According to further embodiments and implementations of the present disclosure, an augmented-reality system configured to assist a subject in the outpatient usage of a medical device is provided. The system includes: (A) a medical device configured to be coupled to a subject, the medical device comprising at least one physiological sensor configured to measure at least one physiological parameter associated with the subject when the medical device is coupled to the subject; and (B) an augmented reality-enabled device comprising a display, at least a first camera having a first field of view, at least a second camera having a second field of view, a wireless communication device, and one or more processors in communication with the display, the wireless communication device, and the first and second cameras, wherein the one or more processors are configured to: (i) receive, via at least the first camera, video data including images of the medical device and/or a packaging of the medical device; (ii) communicate, via the wireless communication device, with a remote content server to transmit the images of the medical device and/or the packaging of the medical device and to receive setup information associated with the medical device, wherein the setup information includes three-dimensional model data associated with the medical device and/or the packaging of the medical device; (iii) create a first composite visual feed from three-dimensional model data and the video data received via the first camera; (iv) display, via the display of the augmented reality-enabled device, the first composite visual feed; (v) receive, via at least the second camera, video data including images of at least a portion of the subject's body; (vi) communicate, via the wireless communication device, with the remote content server to transmit the images of the portion of the subject's body and receive body modeling data associated with the subject's body; (vii) create a second composite visual feed from the received body modeling data and the video data received via at least the second camera; and (viii) display, via the display of the augmented reality-enabled device, the second composite visual feed.

According to still further embodiments and implementations of the present disclosure, a method of using an augmented-reality environment to assist a subject in the usage of a medical device is provided. The method includes: receiving, via at least a first camera of an augmented reality-enabled device, video data comprising images of the medical device and/or a packaging of the medical device; transmitting, via a wireless communication device of the augmented reality-enabled device, the images of the medical device and/or a packaging of the medical device; receiving, via the wireless communication device of the augmented reality-enabled device, setup information associated with the medical device, wherein the setup information comprises three-dimensional model data associated with the medical device and/or the packaging of the medical device; creating, via one or more processors of the augmented reality-enabled device, a first composite visual feed from the three-dimensional model data and the video data received via at least the first camera; and displaying, via a display of the augmented reality-enabled device, the first composite visual feed.

In an aspect, the method further includes: receiving, via at least a second camera of the augmented reality-enabled device, video data comprising images of at least a portion of the subject's body; transmitting, via the wireless communication device, the images of at least the portion of the subject's body to the remote content server; receiving, via the wireless communication device, body modeling data associated with the subject's body from the remote content server; creating, via the one or more processors of the augmented reality-enabled device, a second composite visual feed from the received body modeling data and the video data received via at least the second camera; and displaying, via the display of the augmented reality-enabled device, the second composite visual feed.

In an aspect, the method further includes: detecting, based on the video data received from at least the first camera, completion of a predetermined action associated with the medical device and/or the packaging of the medical device; and automatically switching from receiving video data via at least the first camera to receiving video data via at least the second camera; wherein at least the first camera has a first field of view, and wherein at least the second camera has a second field of view that is different than the first field of view.

In an aspect, the method further includes: tracking, via at least the first camera of the augmented reality-enabled device, a relative position and/or orientation of the medical device and/or the packaging of the medical device; creating, via the one or more processors of the augmented reality-enabled device, a first composite visual feed from the three-dimensional model data and the video data received via at least the first camera, wherein the first composite visual feed is a dynamic composite visual feed that updates a relative position and/or orientation of the three-dimensional model data based on the tracking of the relative position and/or orientation of the medical device and/or the packaging of the medical device; tracking, via at least the second camera of the augmented reality-enabled device, a relative position and/or orientation of the subject's body; and creating, via the one or more processors of the augmented reality-enabled device, a second composite visual feed from the body modeling data and the video data received via at least the second camera, wherein the second composite visual feed is a dynamic composite visual feed that updates a relative position and/or orientation of the body modeling data based on the tracking of the relative position and/or orientation of the subject's body.

These and other aspects of the various embodiments will be apparent from and elucidated with reference to the embodiments described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the various embodiments.

DETAILED DESCRIPTION OF EMBODIMENTS

The present disclosure is related to outpatient usage of medical devices, and more particularly to the usage of medical devices by laypersons in home settings. While technological advances in healthcare services in general and patient monitoring in particular, as well as the demands and resource constraints brought upon by the COVID-19 pandemic, have accelerated the adoption and implementation of remote patient care, it must be appreciated that this has increased the burden on individual patients and their caregivers with respect to the usage of medical devices. It has been observed that this increased burden limits the effectiveness of remote care (including remote patient monitoring) for a number of reasons. For example, patients may feel uncomfortable or lack confidence in using medical devices without the assistance of a trained professional. Furthermore, even when patients and their caregivers attempt to use a medical device, they may not be able to use the medical device in the proper way or consistently in the proper way. Additionally, instructions provided with current medical devices are typically one-size-fits-all, meaning that they are not tailored to individual patients and cannot be adapted to particular features (e.g., skin irritations, etc.) of individual patients. Accordingly, described herein are systems and methods for providing automated support instructions to patients during medical device unboxing and installation via an augmented reality-enabled device.

Figure 1:
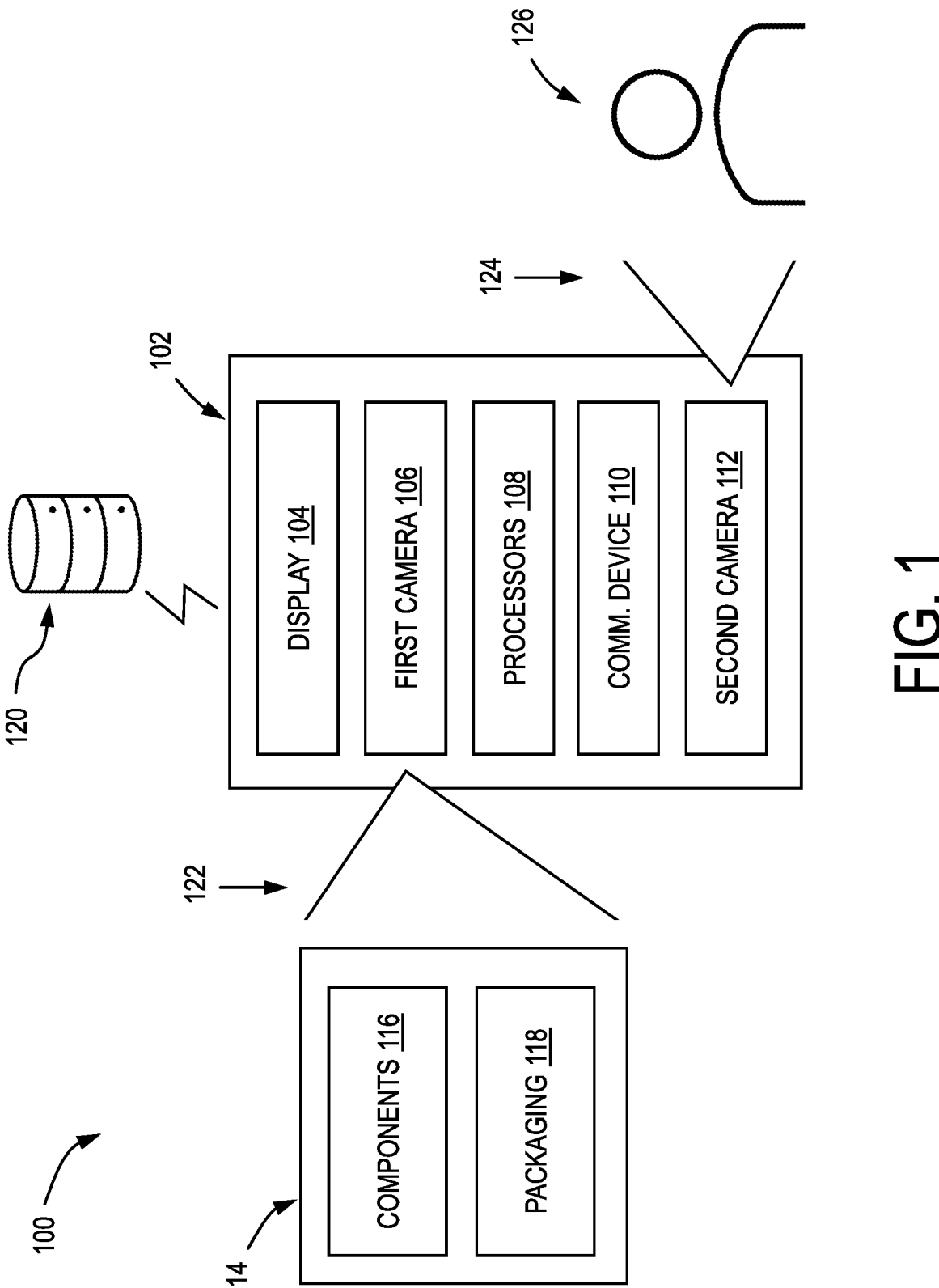
FIG. 1 is a diagram illustrating an augmented reality system for assisting subjects in the usage of a medical device according to aspects of the present disclosure.

Turning to FIG. 1, a system 100 configured to provide automated and patient-specific support instructions to a patient during medical device unboxing or unpackaging and subsequent deployment or installation is illustrated according to certain aspects of the present disclosure. In embodiments, the system 100 includes an augmented reality-enabled device 102 comprising a display 104, at least a first camera 106, and one or more processors 108 configured to perform one or more steps of the methods described herein. In particular embodiments, the one or more processors 108 are configured to: (i) receive, via at least the first camera 106, video data comprising images of a medical device 114 or a portion thereof; (ii) communicate with a remote content server 120 to transmit the images of the medical device 114 and to receive setup information associated with the medical device 114, wherein the setup information comprises three-dimensional model data associated with the medical device 114 or a portion thereof; (iii) create a first composite visual feed from the three-dimensional model data of the setup information and the video data received by at least the first camera 106; and (iv) display, via the display 104, the first composite visual feed.

More particularly, the augmented reality-enabled device 102 (referred to herein as "AR device") may include a communication device 110, such as a wireless communication device, to communicate with the remote content server 120. In embodiments, the AR device may transmit video data comprising images to the remote content server 120 and receive information or data back relevant to the described processes. For example, in embodiments, at least the first camera 106 of the AR device 102 may be used to collect video data comprising images showing the medical device 114 or a portion thereof. In particular embodiments, the video data may comprise images showing one or more components 116 of the medical device 114 and/or the packaging 118 of the medica device 114.

Based on the images of the video data collected by at least the first camera 106, the AR device 102 and/or the remote content server 120 may identify setup information corresponding to the medical device 114 shown in the video data. For example, in some embodiments, images of the video data collected by at least the first camera 106 may be transmitted to the remote content server 120 for image processing, and based on that processing, the remote content server 120 may identify the specific type or model of medical device shown in the images, evaluate a status of the unboxing/unpackaging processing (e.g., information about the packaging 118), and/or generate additional setup information as described in more detail below. In other embodiments, the AR device 102 itself may be configured to identify, based on the video data received from at least the first camera 106, the specific type of medical device 114 and/or a status of the unboxing process. In still further embodiments, the medical device 114 and/or its packaging 118 may include a scannable code (e.g., a QR code, bar code, etc.) that specifically identifies setup information associated with the medical device 114.

As described herein, it should be appreciated that the medical device 114 may be delivered in packaging 118 that contains one or more boxes, pouches, and/or the like, and each packaging may contain one or more components 116 of the medical device that may need to be assembled by a patient or caregiver. Accordingly, the unboxing or unpackaging process of the medical device 114 described herein can include the assembly of one or more components 116 to form a useable medical device 114. In embodiments, the medical device 114 includes at least one physiological sensor configured to measure at least one physiological parameter associated with the subject 126 when the medical device 114 is coupled to the subject 126 or attached to the subject's body. However, it should also be appreciated that the medical device 114 must be properly coupled with the subject 126. Accordingly, the systems and methods described herein enable improved accuracy and compliance with remote patient monitoring devices by guiding patients in the proper placement of these devices.

In embodiments, once the medical device 114 is identified, the AR device 102 may receive setup information from the remote content server 120 that contains three-dimensional model data associated with the medical device 114 and/or a portion thereof. For example, the remote content server 120 may contain a repository of information related to a plurality of medical devices 114 and/or the packaging 118 used for a plurality of different types of medical devices 114, including but not limited to their physical dimensions, how items are secured together, which items or components are included with the packaging, and the like. In embodiments, the remote content server 120 may also contain a repository of three-dimensional model data associated with each of these medical devices 114, their components 114, and/or their packaging 118. In some embodiments, the three-dimensional ("3D") model data may be stored as a 3D model file that includes the information about the model's geometry, surface texture, scene details, and/or any associated animations. In particular embodiments, the 3D model file is a gLTF file, a GLB file, an FBX file, an USDZ file, a USD file, a COLLADE file, an STL file, an OBJ file, a FBX file, a DAE file, a 3DS file, an IGES file, a STEP file, a VRML file, a X3D file, an AMF file, a 3MF file, a BLEND file, a DWG file, and/or the like.

In embodiments, the one or more processors 108 of the AR device 102 may be configured to receive setup information from the remote content server 120 that includes the 3D model data that corresponds to the identified medical device 114 and/or a portion thereof. In further embodiments, the setup information includes one or more steps for unpackaging and/or assembling the components 116 of the medical device 114, including but not limited to, animations associated with the 3D model data that visually demonstrate how to unpackage and/or assembly the components 116 of the medical device 114. In embodiments, the setup information received from the remote content server 120 can also include one or more alerts (e.g., visual alerts, auditory alerts, haptic alerts, and/or the like).

Based on the received setup information, the one or more processors 108 of the AR device 102 can be configured to generate a first composite visual feed using the 3D model data and the video data received via at least the first camera 106. In embodiments, generating the composite visual feed involves superimposing the 3D model of the medical device 114 and/or a portion thereof onto the medical device 114 or a portion thereof as it is shown in the video feed collected by the first camera 106. In some embodiments, the composite visual feed may be static, meaning that a still image from the video data showing the medical device 114 is used. In such embodiments, a single relative position and orientation of the medical device 114 (or a portion thereof) may be tracked and determined, and the corresponding 3D model is positioned such that it is superimposed onto the static image.

In other embodiments, the composite visual feed may be dynamic, meaning that a live or near real-time video feed is collected by at least the first camera 106 and the corresponding 3D model is continuously positioned such that it is superimposed onto the live/near real-time video feed. Put another way, the one or more processors 108 of the AR device 102 may be configured, in some embodiments, to track the relative position and/or orientation of the medical device 114 or a portion thereof (e.g., the components 116 and/or the packaging 118) within the video data captured by at least the first camera 106, and to create a first composite visual feed that is a dynamic composite visual feed. In such embodiments, the relative position and/or orientation of the 3D model superimposed in the composite visual feed may be updated as the relative position and/or orientation of the corresponding medical device 114 or a portion thereof is changed. For example, in particular embodiments, the composite visual feed may be updated to follow along with a patient who is picking up, moving, or otherwise manipulating the medical device 114 (i.e., unboxing and/or assembling the medical device 114).

In embodiments, the AR device 102 further comprises at least a second camera 112 that has a different field of view 124 than at least the first camera 106. That is, in embodiments, at least the first camera 106 has a first field of view 122 while the at least the second camera 112 has a second field of view 124 that is different from the first field of view

122 of at least the first camera 106. In some embodiments, the first and second fields of view 122, 124 do not overlap, or are mutually exclusive. For example, in some embodiments, the first camera 106 may be a rear-facing camera of the AR device 102 while the second camera 112 is a front-facing camera of the AR device 102, resulting in fields of view 122, 124 that do not overlap.

In embodiments having at least a second camera 112, the one or more processors 108 of the AR device 102 may be configured to: (i) receive, via at least the second camera 112, video data; (ii) communicate with the remote content server 120 to transmit the video data and/or a portion thereof and receive body modeling data associated with a subject 126; (iii) create a second composite visual feed from the received body modeling data and the video data received from at least the second camera 112; and (iv) display, via the display 104, the second composite visual feed.

In particular embodiments, the video data collected by at least the second camera 112 can comprise images of at least a portion of a subject's body 126. For example, in some embodiments, the subject or user 126 of the AR device 102 may intend to personally use the medical device 114, such as in the case of a wearable patient monitoring device. As such, the subject 126 will need to be instructed on how to position the wearable device. In embodiments, at least the second camera 112 of the AR device 102 can be used to capture images of the portion of the body where the subject 126 must wear the medical device 114. In some embodiments, for example, the medical device 114 may be a mobile cardiac outpatient telemetry (MCOT) device, which must be secured to a portion of the subject's chest in order to accurately obtain cardiovascular readings.

Based on the images of the video data collected by at least the second camera 112, the AR device 102 and/or the remote content server 120 may identify installation features corresponding to the subject 126 shown in the video data collected by at least the second camera 112. For example, in some embodiments, images of the video data collected by at least the second camera 112 may be transmitted to the remote content server 120 for image processing, and based on that processing, the remote content server 120 may identify a status of the subject 126 or a portion thereof, including but not limited to any conditions of the subject 126. In specific embodiments, the remote content server 120 may determine whether the portion of the subject 126 is ready for application of the medical device 114 (i.e., determining whether the area is exposed, is clean, is shaven, etc.). In some embodiments, the AR device 102 itself may be configured to identify, based on the video data received from at least the second camera 112, the installation information associated with the medical device 114 and the subject 126.

In further embodiments, the installation features may also include one or more measurements associated with the subject 126 that can be used to generate a three-dimensional digital model of the subject 126 or a portion thereof in the form of body modeling data. In embodiments, the AR device 102 may receive the body modeling data associated with the subject 126 from the remote content server 120. In some embodiments, the remote content server 120 may contain a repository of body modeling data that is used to match with the installation features associated with a subject 126, or may generate new body modeling data for each subject 126 based on the installation features. In some embodiments, the body modeling data may be stored as a 3D model file that includes the information about the model's geometry, surface texture, scene details, and/or any associated animations. In particular embodiments, the 3D model file is a gLTF file, a GLB file, an FBX file, an USDZ file, a USD file, a COLLADE file, an STL file, an OBJ file, a FBX file, a DAE file, a 3DS file, an IGES file, a STEP file, a VRML file, a X3D file, an AMF file, a 3MF file, a BLEND file, a DWG file, and/or the like.

In certain embodiments, the body modeling data may include one or more animations and/or instructions for preparing the body of the subject 126 for application of the medical device 114. For example, in some embodiments, the body modeling data may include one or more animations and/or instructions for shaving, cleaning, or otherwise evaluating portions of the body of the subject 126 in accordance with the intended use of the medical device 114. In embodiments, the installation information received from the remote content server 120 can also include one or more alerts (e.g., visual alerts, auditory alerts, haptic alerts, and/or the like).

In embodiments, the one or more processors 108 of the AR device 102 can be configured to generate a second composite visual feed based on the video data received via at least the second camera 112 and the installation information and/or body modeling data. In some embodiments, generating the second composite visual feed involves superimposing the digital model of the subject 126 onto the images of the subject 126 within the data feed. In embodiments, generating the second composite visual feed may also involve superimposing the digital model of the medical device 114 onto the images of the medical device 114 shown in the video data captured using at least the second camera 112. That is, in some embodiments, both the subject 126 and the medical device 114 may be shown in the video data captured using at least the second camera 112 (for example, when the subject 126 goes to couple of the medical device 114 to their body). Accordingly, the second composite visual feed may include superimposing a digital model of the medical device 114 onto the body of the subject 126 and/or animating the proper placement of the medical device 114 onto the body of the subject 126.

In embodiments, the second composite visual feed may be static, meaning that a still image from the video data showing the subject 126 is used. In such embodiments, a single relative position and orientation of the subject 126 may be tracked and determined, and the corresponding body model is positioned such that it is superimposed onto the static image.

In other embodiments, the second composite visual feed may be dynamic, meaning that the visual feed includes a plurality of images showing the subject 126 where the subject 126 may or may not be moving. In some examples, the composite visual feed may be based on a live or near real-time video feed that is collected by at least the second camera 112. Accordingly, the one or more processors 108 of the AR device 102 may be configured to track the relative position and/or orientation of the subject 126 within the video data captured by at least the second camera 112, and to create a second composite visual feed such that the relative position and/or orientation of the digital body model of the subject 126 being superimposed in the composite visual feed is updated as the relative position and/or orientation of the subject 126 changes.

In embodiments, the one or more processors 108 of the AR device 102 may be configured to automatically switch between using at least the first camera 106 and at least the second camera 112. That is, the AR device 102 may be configured to automatically switch from receiving video data via at least the first camera 106 to receiving video data via at least the second camera 112, and/or vice versa. In certain embodiments, when the AR device 102 switches from receiving video data via one camera 106, 112 to receiving video data via another camera 106, 112, the AR device 102 may also automatically switch from displaying a composite visual feed based on the video data collected by the original camera 106, 112 to displaying a composite visual feed based on the video data by the subsequent camera 106, 112. For example, the one or more processors 108 of the AR device 102 can be configured to receive video data via at least a first camera 106, generate a first composite visual feed using at least the video data from the first camera 106, display the first composite visual feed on the display 104 of the AR device 102, and then automatically switch to receive video data via at least the second camera 112, generate a second composite visual feed using at least the video data from the second camera 112, and display the second composite visual feed on the display 104 of the AR device 102.

In certain embodiments, the AR device 102 may be configured to switch between two or more cameras 106, 112 having different fields of view 122, 124 based on one or more triggering events. That is, in embodiments, the one or more processors 108 are configured to detect the occurrence of one or more events, for example, by analyzing the video data received from either the first and/or second cameras 106, 112. In some embodiments, the occurrence of one or more events can include the completion of a predetermined action or task, such as unboxing or unpackaging the medical device 114 and/or assembling the components 116 of the medical device 114.

In specific embodiments, one of the triggering events that may be detected is the assembled medical device 114 leaving the field of view 122 of at least the first camera 106. For example, when the subject 126 completes the assembly of the medical device 114, the subject 126 may move the medical device 114 towards their body such that the medical device 114 leaves the field of view 122 of at least the first camera 106. Such an event may be detected by tracking the relative position and/or orientation of the medical device 114 as described herein, and upon detection, the AR device 102 may automatically switch to using at least the second camera 112. In further embodiments, the detected event may also be indicative of the medical device 114 entering the field of view 124 of at least the second camera 112.

Figure 2:
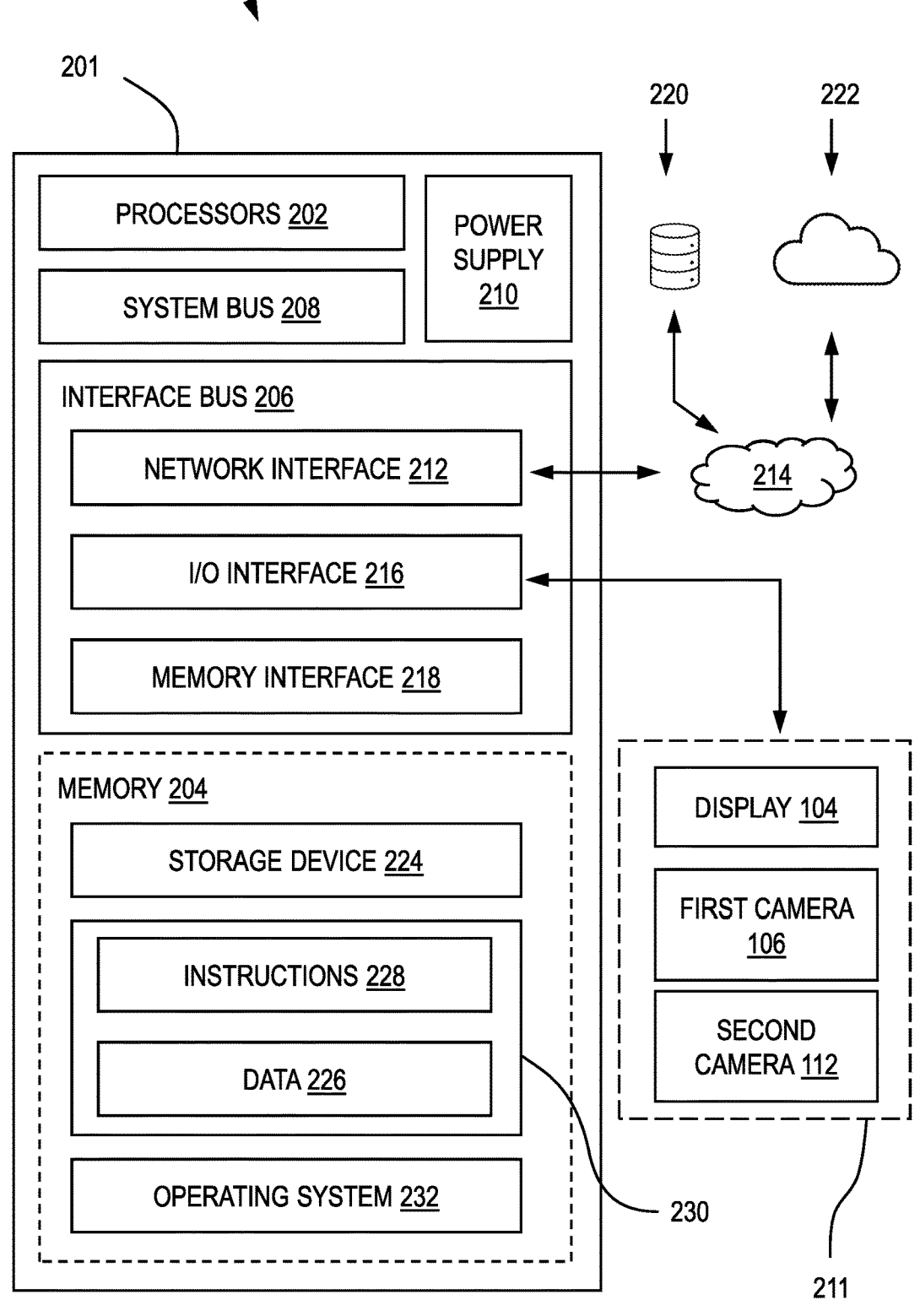
FIG. 2 is a block diagram of an augmented reality-enabled device for configured to assist subjects in the usage of a medical device according to aspects of the present disclosure.
Figure 3:
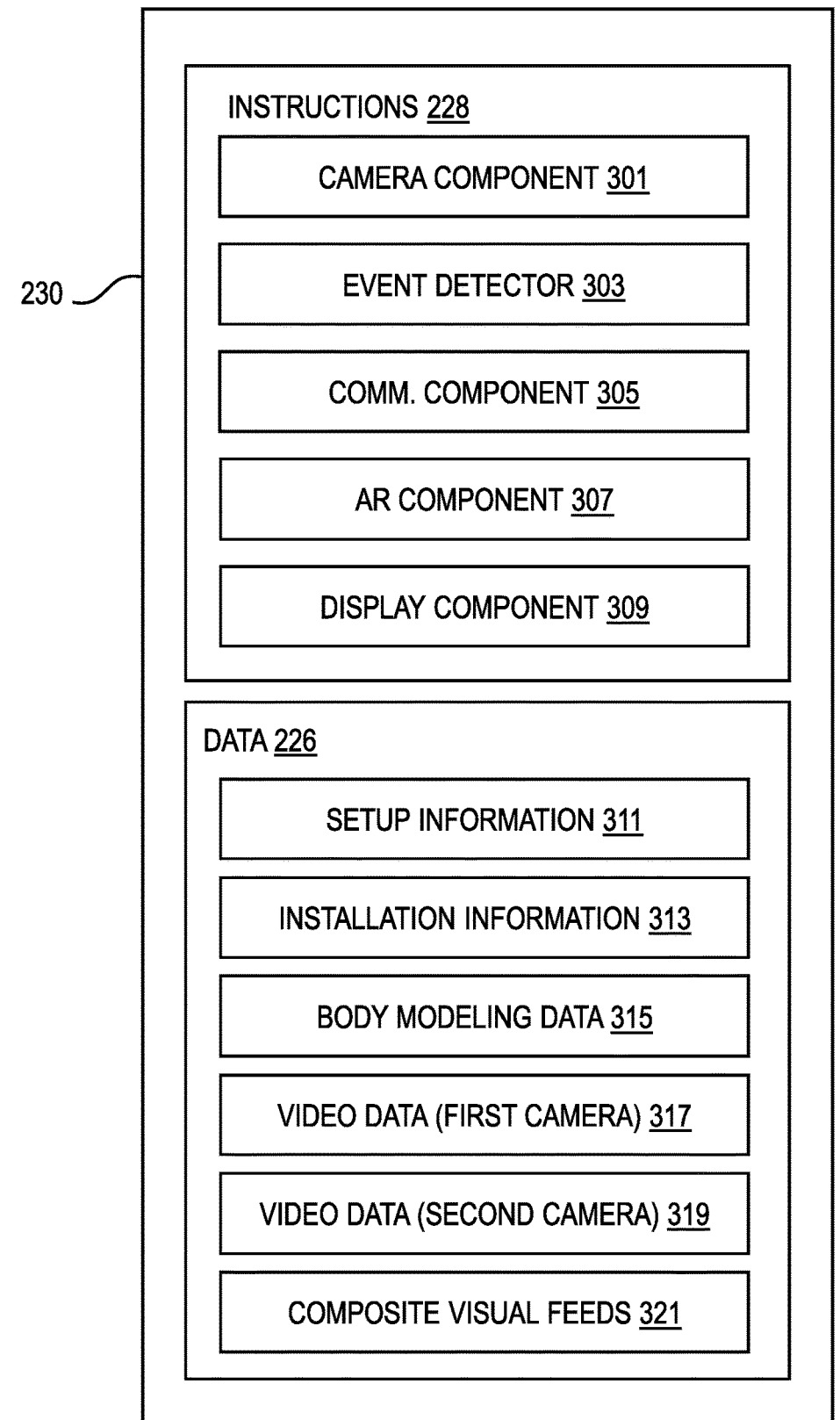
FIG. 3 is a block diagram of an augmented reality user guidance package illustrated according to aspects of the present disclosure.

With reference to FIG. 2 and FIG. 3, these and other features are described in accordance with further aspects of the present disclosure. In particular, as shown in FIG. 2, a system 100 configured to provide automated and patient-specific support instructions to a patient during medical device unboxing, unpackaging, deployment, and/or installation is illustrated according to additional aspects of the present disclosure. The system 100 can include an augmented reality-enabled device 201 comprising one or more processors 202, machine-readable memory 204, and an interface bus 206, all of which may be interconnected and/or communicate through a system bus 208 containing conductive circuit pathways through which instructions (e.g., machine-readable signals) may travel to effectuate communication, tasks, storage, and the like. The AR device 201 may be connected to a power source 210, which can include an internal power supply and/or an external power supply.

The one or more processors 202 may include a high-speed data processor adequate to execute the program components described herein and/or various specialized processing units as may be known in the art. In some examples, the one or more processors 202 may be a single processor, multiple processors, or multiple processor cores on a single die.

In some examples, the interface bus 206 may include a network interface 212 configured to connect the AR device 201 to a communications network 214, an input/output ("I/O") interface 216 configured to connect and communicate with one or more integrated or removable devices 211 (e.g., a user interface, a display 104, one or more cameras 106, 112, etc.), and/or a memory interface 218 configured to accept, communication, and/or connect to a number of machine-readable memory devices (e.g., memory 204).

The network interface 212 may operatively connect the AR device 201 to a communications network 214, which can include a direct interconnection, the Internet, a local area network ("LAN"), a metropolitan area network ("MAN"), a wide area network ("WAN"), a wired or Ethernet connection, a wireless connection, and similar types of communications networks, including combinations thereof. In some examples, AR device 201 may communicate with one or more remote/cloud-based servers 220, cloud-based services 222, and/or remote devices via the communications network 214 and the network interface 212.

The memory 204 can be variously embodied in one or more forms of machine-accessible and machine-readable memory, including transitory and non-transitory memory. In some examples, the memory 204 includes a storage device 224 comprises one or more types of memory. For example, the storage device 224 can include, but is not limited to, a non-transitory storage medium, a magnetic disk storage, an optical disk storage, an array of storage devices, a solid-state memory device, and the like, including combinations thereof.

Generally, the memory 204 is configured to store data/information 226 and instructions 228 that, when executed by the one or more processors 202, causes the AR device 102 to perform one or more tasks. In particular examples, the memory 204 includes a user guidance package 230 that comprises a collection of program components, database components, and/or data. Depending on the particular implementation, the user guidance package 230 may include software components, hardware components, and/or some combination of both hardware and software components.

With reference to FIG. 3, the user guidance package 230 may include, but is not limited to, instructions 228 having one or more software packages configured to perform one or more steps of the methods described herein. These software packages may be incorporated into, loaded from, loaded onto, or otherwise operatively available to and from the AR device 102. Put another way, the user guidance package 230 and/or one or more software packages may be incorporated into, loaded from, loaded onto, or otherwise operatively available to an AR device 102. In some examples, the user guidance package 230 and/or one or more individual software packages may be stored in a local storage device 224. In other examples, the user guidance package 230 and/or one or more individual software packages may be loaded onto and/or updated from a remote server 220 via the communications network 214.

In particular embodiments, the user guidance package 230 can include, but is not limited to, instructions 228 having a camera component 301, an event detector 303, a communications component 305, an augmented reality ("AR") component 307, and/or a display component 309. These components may be incorporated into, loaded from, loaded onto, or otherwise operatively available to and from the AR device 102.

The camera component 301 can be a stored program component that is executed by at least one processor, such as the one or more processors 202 of the AR device 102. In particular, the camera component 301 can be configured to operate one or more cameras 106, 112 of the AR device 102, 201 in order to receive video data 317, 319 comprising a plurality of images.

The event detector 303 can be a stored program component that is executed by at least one processor, such as the one or more processors 202 of the AR device 102. In particular, the event detector 303 can be configured to analyze the video data 317, 319 obtained using one or more cameras 106, 112 in order to detect the occurrence of one or more events. Put another way, the event detector 303 may be configured to identify one or more objects shown in the images of the video data 317, 319, track the relative positions and/or orientations of the one or more objects, and make one or more inferences based on the objects identified and/or changes in their relative positions and/or orientations.

For example, as described herein, the events-of-interest can include, but are not limited to, identifying one or more actions taken to unbox a medical device 114, identifying one or more actions taken to assemble a medical device 114, identifying whether a medical device 114 has been assembled, identifying whether the medical device 114 has left a field of view of a camera (e.g., field of view 122 of at least the first camera 106), identifying whether the medical device 114 has entered the field of view of another camera (e.g., field of view 122 of at least the second camera 112), identifying a subject 126 that intends to use the medical device 114, identifying whether the subject 126 or a portion thereof is prepared for applying the medical device 114, identifying one or more actions taken to prepare the subject 126 for the application of the medical device 114, and/or the like.

The communications component 305 can be a stored program component that is executed by at least one processor, such as the one or more processors 202 of the AR device 102. In particular, the communications component 305 can be configured to connect with one or more remote servers 120, 220, and/or remote servers 222 via a communications network 214 in order to send and receive data. In embodiments, the communications component 305 can be configured to transmit video data 317, 319 collected by one or more cameras 106, 112 to a remote content server 120, for example, and to receive setup information 311, installation information 313, and/or body modeling data 315 from the remote content server 120.

As described above, the setup information 311 can include, but is not limited to, 3D model data associated with one or more medical devices 114, as well as instructions having one or more steps for unpackaging and/or assembling the medical device 114. In embodiments, the setup information 311 may also include 3D model data associated with the medical device and/or its packaging. The installation information 313 can include, but is not limited to, instructions having one or more steps for preparing and/or attaching the medical device 114 onto an attachment site located on the subject 126. In embodiments, the installation information 313 can also include body modeling data 315 associated with the body of the subject 126.

The augmented reality ("AR") component 307 can be a stored program component that is executed by at least one processor, such as the one or more processors 202 of the AR device 102. In particular, the AR component 307 can be configured to generate one or more composite visual feeds 321 based on a combination of video data 317, 319 and 2D or 3D modeling data 315. In embodiments, a composite visual feed 321 can be generated by registering the relative position and/or orientation of one or more objects within video data 317, 319 with a 2D or 3D model 315 and generating a visual feed 321 where the 2D or 3D modeling data 315 is superimposed onto the corresponding one or more objects within video data 317, 319. In embodiments, one or more of the composite visual feeds 321 may be static, meaning that a single still image from a set of video data 317, 319 showing one or more objects is used. In such embodiments, the relative position and orientation of the one or more objects may be determined once, and the corresponding model data 315 is positioned such that it is superimposed onto the static image. In other embodiments, one or more composite visual feeds 321 may be dynamic, meaning that the visual feed 321 includes a plurality of images showing one or more objects as that are moved or manipulated by a subject 126. In some examples, the composite visual feed 321 may be based on a live or near real-time video feed that is collected by one or more cameras 106, 112. Accordingly, the AR component 307 can be configured to update the relative position and/or orientation of one or more digital models being superimposed onto one or more objects in the composite visual feed 321 as the one or more objects are moving.

The display component 309 can be a stored program component that is executed by at least one processor, such as the one or more processors 202 of the AR device 102. In particular, the display component 309 can be configured to operate the display 104 of the AR device 102, 201, including being able to cause the generated composite visual feeds 321 to be displayed on the display 104 at the appropriate times.

Returning to FIG. 2, the AR device 201 may also include an operating system component 232, which may be stored in the memory 204. The operating system component 232 may be an executable program facilitating the operation of the system 200 and/or the AR device 201. Typically, the operating system component 232 can facilitate access of the I/O interface, network interface, and memory interface, and can communicate with other components of the system 200.

Also provided herein are methods of providing automated and patient-specific support instructions to a patient during medical device unboxing, unpackaging, deployment, and/or installation. In embodiments, the methods comprise: (i) receiving, via at least a first camera of an augmented reality-enabled device, wherein the video data comprises images of the medical device and/or a packaging of the medical device; (ii) transmitting, via a wireless communication device of the augmented reality-enabled device, the images of the medical device and/or a packaging of the medical device; (iii) receiving, via the wireless communication device of the augmented reality-enabled device, setup information associated with the medical device, wherein the setup information comprises three-dimensional model data associated with the medical device and/or the packaging of the medical device; (iv) creating, via one or more processors of the augmented reality-enabled device, a first composite visual feed from the three-dimensional model data and the video data received via at least the first camera; and (v) displaying, via a display of the augmented reality-enabled device, the first composite visual feed. In some embodiments, the methods also include: (vi) receiving, via at least a second camera of the augmented reality-enabled device, wherein the video data comprises images of at least a portion of the subject's body; (vii) transmitting, via the wireless communication device, the images of at least the portion of the subject's body to the remote content server; (viii) receiving, via the wireless communication device, body modeling data associated with the subject's body from the remote content server; (ix) creating, via the one or more processors of the augmented reality-enabled device, a second composite visual feed from the received body modeling data and the video data received via at least the second camera; and (x) displaying, via the display of the augmented reality-enabled device, the second composite visual feed.

Figure 4A:
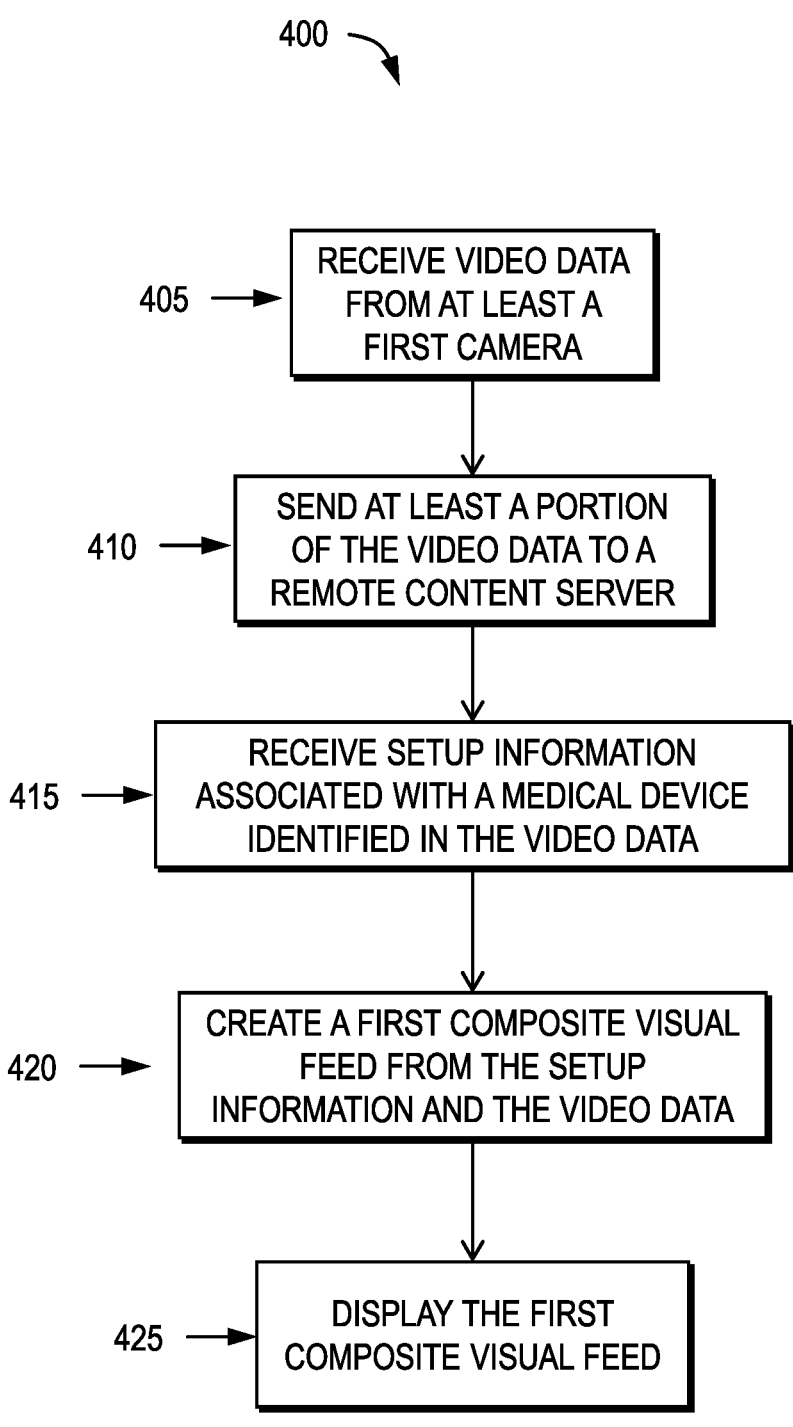
FIG. 4A is a flowchart illustrating a method of using an augmented-reality environment to assist a subject in the usage of a medical device according to aspects of the present disclosure.

For example, with reference to FIG. 4A, an exemplary method 400 of providing patient-specific support instructions to a patient during medical device unboxing, unpackaging, deployment, and/or installation is illustrated according to various aspects of the present disclosure. As shown, the method 400 includes: in a step 405, receiving video data from at least a first camera; in a step 410, sending at least a portion of the video data to a remote content server; in a step 415, receiving setup information associated with a medical device identified in the video data; in a step 420, creating a first composite visual feed from the setup information and the video data; and, in a step 425, displaying the first composite visual feed.

More specifically, in the step 405, the method 400 can include receiving video data comprising a plurality of images from at least a first camera of an augmented reality-enabled device. In embodiments, the video data can include images showing a medical device, components of a medical device, and/or the packaging of a medical device. That is, the medical device, components of a medical device, and/or the packaging of a medical device are within the field of view of at least the first camera of the AR device.

In the step 410, the method 400 can include transmitting the video data received from at least the first camera and/or a portion thereof to a remote content server. In embodiments, video data transmitted to the remote content server can include one or more images showing the medical device, components of a medical device, and/or the packaging of a medical device. In further embodiments, the video data and/or a portion thereof may be transmitted via a wireless communications device of the AR device.

In the step 415, the method 400 can include receiving, from the remote content server, setup information associated with the medical device, components of a medical device, and/or the packaging of a medical device. As described above, the video data received by at least the first camera can be analyzed either by the remote content server and/or the AR device in order to identify different parameters and/or conditions of the medical device, components of a medical device, and/or the packaging of a medical device. Based thereon, the remote content server may transmit setup information that corresponds to the identified medical device, components of a medical device, and/or packaging of a medical device. In particular embodiments, the setup information includes at least modeling data associated with the medical device, components of a medical device, and/or the packaging of a medical device. In some embodiments, the modeling data is three-dimensional modeling data, as described above.

In the step 420, the method 400 can include creating a first composite visual feed from the model data of the setup information and the video data received by at least the first camera. In embodiments, the first composite visual feed may be created by superimposing the model data of one or more objects onto one or more objects identified within the video data. In embodiments, the composite visual feed may be a static or a dynamic visual feed, as described above.

In the step 425, the method 400 can include displaying the first composite visual feed. In embodiments, the first composite visual feed may be displayed on a display of the AR device. In particular embodiments, the first composite visual feed that is displayed may be static such that moving the AR device and/or at least the first camera does not change the display. In other embodiments, the first composite visual feed that is displayed may be dynamic, meaning that moving the AR device changes the field of view of at least the first camera and the first composite visual feed is updated accordingly.

Figure 4B:
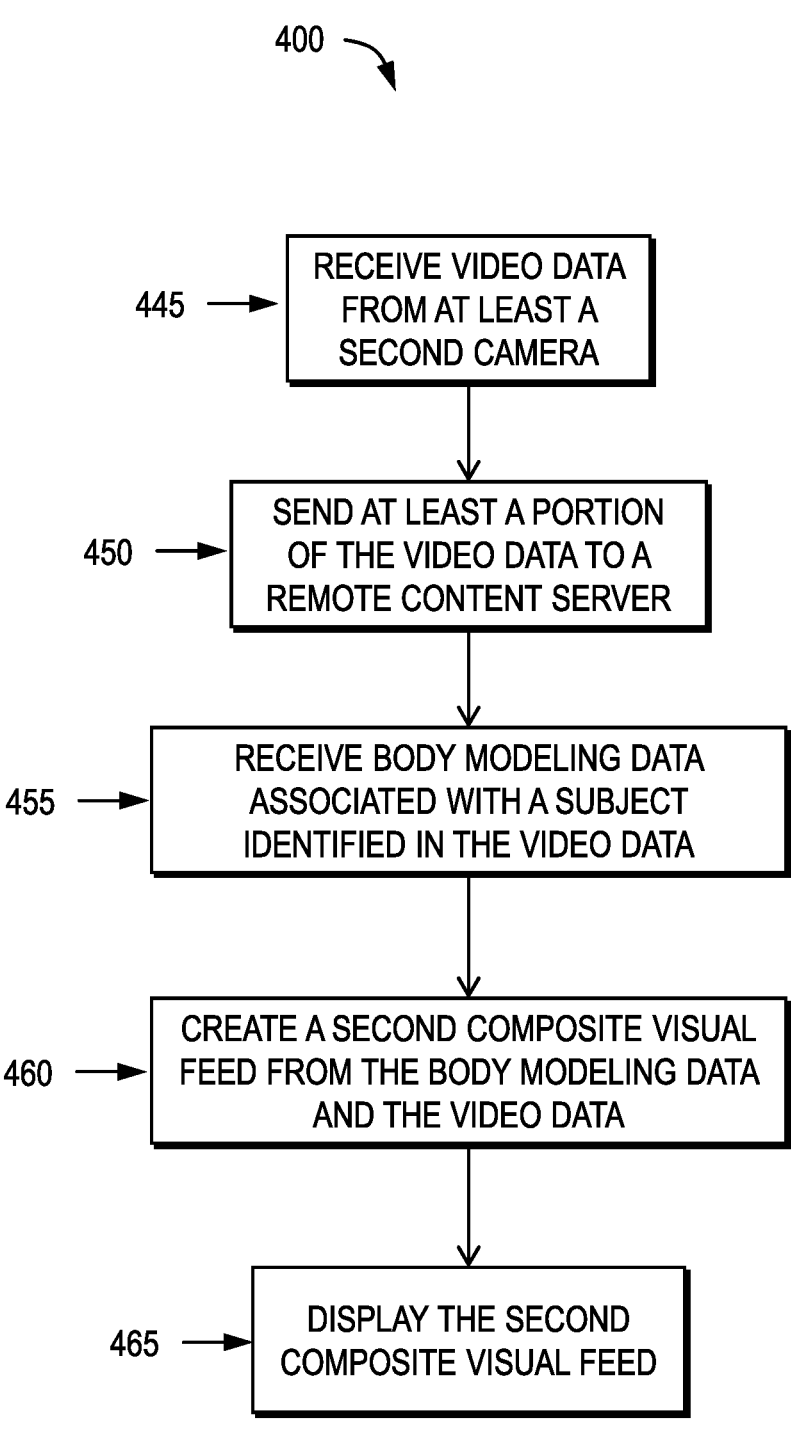
FIG. 4B is another flowchart illustrating a method of using an augmented-reality environment to assist a subject in the usage of a medical device according to further aspects of the present disclosure.

With reference to FIG. 4B, the method 400 can further include: in a step 445, receiving video data from at least a second camera; in a step 450, sending at least a portion of the video data to a remote content server; in a step 455, receiving body modeling data associated with a subject identified in the video data; in a step 460, creating a second composite visual feed from the body modeling data and the video data; and, in a step 465, displaying the second composite visual feed.

More specifically, in the step 445, the method 400 can include receiving video data comprising a plurality of images from at least a second camera of the AR device. In embodiments, at least the second camera has a field of view that is different from the field of view of at least the first camera, as described above. The video data collected by at least the second camera may include images showing a subject (such as a patient) and/or a portion thereof. For example, the subject may be a patient undergoing remote patient monitoring using a mobile cardiac outpatient telemetry (MCOT) device, and the video data collected by at least the second camera may include images showing the chest or upper torso of the subject. In particular embodiments, the portion of the subject captured by at least the second camera can be a region of interest (i.e., where the medical device may be appropriately placed).

In the step 450, the method 400 can transmitting the video data received from at least the second camera and/or a portion thereof to a remote content server. In embodiments, the video data transmitted to the remote content server can include one or more images showing the subject or a portion thereof. In further embodiments, the video data and/or a portion thereof may be transmitted via a wireless communications device of the AR device.

In the step 455, the method 400 can include receiving, from the remote content server, installation information comprising body modeling data. As described above, the video data received by at least the second camera can be analyzed either by the remote content server and/or the AR device in order to identify different parameters and/or conditions of the subject shown in the video data. In particular embodiments, the installation information includes at least body modeling data generated and/or selected based on the subject identified within the video data.

In the step 460, the method 400 can include creating a second composite visual feed from the modeling data of the installation information and the video data received by at least the second camera. In embodiments, the second composite visual feed may be created by superimposing the model data of one or more objects onto subject identified in the video data. For example, a wireframe model torso may be superimposed over the torso of the subject identified in the video data. In embodiments, the composite visual feed may be a static or a dynamic visual feed, as described above.

In the step 465, the method 400 can include displaying the second composite visual feed. In embodiments, the second composite visual feed may be displayed on a display of the AR device. In particular embodiments, the second composite visual feed that is displayed may be static such that moving the AR device and/or at least the second camera does not change the display. In other embodiments, the second composite visual feed that is displayed may be dynamic, meaning that moving the AR device changes the field of view of at least the second camera and the second composite visual feed is updated accordingly.

Figure 4C:
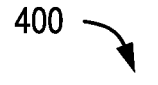
FIG. 4C is a still another flowchart illustrating a method of using an augmented-reality environment to assist a subject in the usage of a medical device according to aspects of the present disclosure.
Figure 4C:
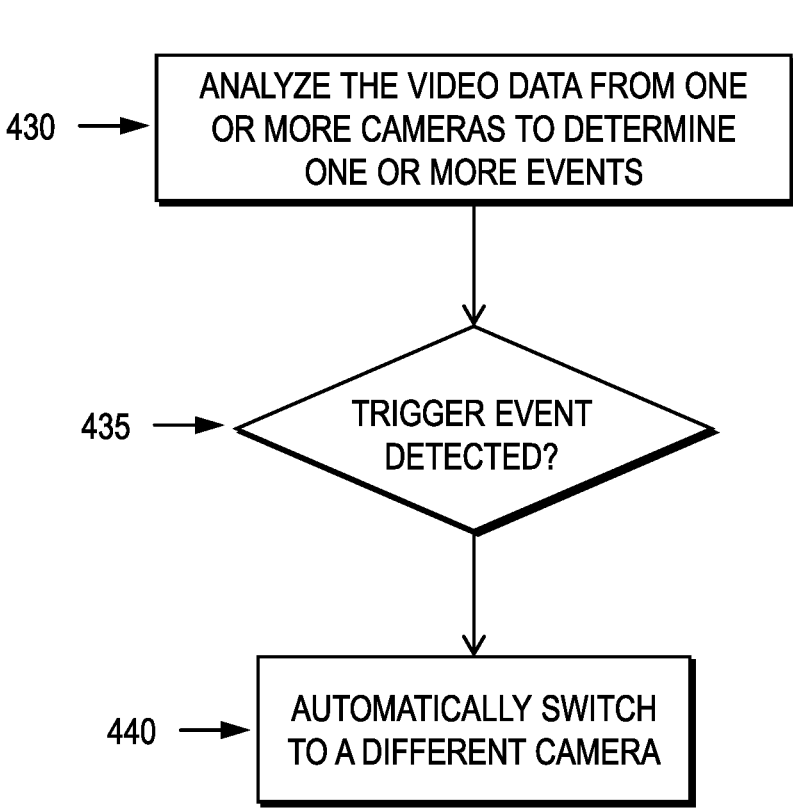

Turning to FIG. 4C, the method 400 can further include: in a step 430, analyzing the video data from one or more cameras of the AR device in order to determine the occurrence of one or more events; in a step 435, determining whether a triggering event has been detected; and if so, automatically switching to a different camera setup in a step 440.

More specifically, in the step 430, the AR device may be configured to analyze the video data from the one or more cameras in order to determine the occurrence of one or more events. In some embodiments, the occurrence of one or more events can include the completion of a predetermined action or task, such as unboxing or unpackaging the medical device and/or assembling the components of the medical device. For example, as described herein, the events-of-interest can include, but are not limited to, identifying one or more actions taken to unbox a medical device, identifying one or more actions taken to assemble a medical device, identifying whether a medical device has been assembled, identifying whether the medical device has left a field of view of a camera (e.g., field of view of at least the first camera), identifying whether the medical device has entered the field of view of another camera (e.g., field of view of at least the second camera), identifying a subject that intends to use the medical device, identifying whether the subject or a portion thereof is prepared for applying the medical device, identifying one or more actions taken to prepare the subject for the application of the medical device, and/or the like.

In specific embodiments, one of the triggering events that may be detected is the assembled medical device leaving the field of view of at least the first camera. For example, when the subject completes the assembly of the medical device, the subject may move the medical device towards their body such that the medical device leaves the field of view of at least the first camera. Such an event may be detected by tracking the relative position and/or orientation of the medical device as described herein.

In the step 435, the method 400 can include determining whether one or more triggering events have occurred. If so, the method 400 may proceed to the step 440, wherein the AR device automatically switches from using one set of cameras to a different set of cameras. For example, upon detection of a qualifying triggering event by analyzing video data being collected by at least the first camera, the AR device may automatically switch to using at least the second camera. In other embodiments, the AR device may automatically switch to using at least the first camera if a qualifying triggering event is detected while analyzing the video data collected by at least the second camera.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

As used herein, although the terms first, second, third, etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

Unless otherwise noted, when an element or component is said to be "connected to," "coupled to," or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

It should also be understood that, unless clearly indicated to the contrary, in any methods claimed herein that include more than one step or act, the order of the steps or acts of the method is not necessarily limited to the order in which the steps or acts of the method are recited.

The above-described examples of the described subject matter can be implemented in any of numerous ways. For example, some aspects can be implemented using hardware, software or a combination thereof. When any aspect is implemented at least in part in software, the software code can be executed on any suitable processor or collection of processors, whether provided in a single device or computer or distributed among multiple devices/computers.

The present disclosure can be implemented as a system, a method, and/or a computer program product at any possible technical detail level of integration. The computer program product can include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium comprises the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, comprising an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, comprising a local area network (LAN) or a wide area network (WAN), or the connection can be made to an external computer (for example, through the Internet using an Internet Service Provider). In some examples, electronic circuitry comprising, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to examples of the disclosure. It will be understood that each block of the flowchart illustrations and/or block diagrams, and combinations of blocks in the flowchart illustrations and/or block diagrams, can be implemented by computer readable program instructions.

The computer readable program instructions can be provided to a processor of a, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture comprising instructions which implement aspects of the function/act specified in the flowchart and/or block diagram or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various examples of the present disclosure. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Other implementations are within the scope of the following claims and other claims to which the applicant can be entitled.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A system for providing automated support instructions to a subject during assembly and installation of a medical device configured to be coupled to a subject in an outpatient setting, the medical device comprising at least one physiological sensor configured to measure at least one physiological parameter associated with the subject when the medical device is coupled to the subject, the system comprising:

an augmented reality-enabled device comprising a display, at least a first camera, and one or more processors in communication with the display and at least the first camera, wherein the one or more processors are configured to:

receive, via at least the first camera, video data comprising images of the medical device and/or a packaging of the medical device;

communicate with a remote content server to transmit the images of the medical device and/or the packaging of the medical device and to receive setup information associated with the medical device, wherein the setup information comprises three-dimensional model data associated with the medical device and/or the packaging of the medical device;

create a first composite visual feed from the three-dimensional model data and the video data received via at least the first camera; and display, via the display of the augmented reality-enabled device, the first composite visual feed.

2. The system of claim 1, wherein the setup information further comprises instructions having one or more steps for unpackaging and/or assembling the medical device.

3. The system of claim 2, wherein the one or more processors of the augmented reality-enabled device are further configured to:

create a first composite visual feed from the three-dimensional model data and the video data received via at least the first camera, wherein the first composite visual feed includes at least a portion of the instructions having one or more steps for unpackaging and/or coupling the medical device to the subject; and display, via the display of the augmented reality-enabled device, the first composite visual feed comprising at least the portion of the instructions.

4. The system of claim 1, wherein the augmented reality-enabled device further comprising at least a second camera, the first camera having a first field of view and the second camera having a second field of view that is different from the first field of view, and wherein the one or more processors of the augmented reality-enabled device are further configured to:

receive, via at least the second camera, video data comprising images of the medical device and at least a portion of the subject's body;

communicate with the remote content server to transmit the images of the portion of the subject's body and receive body modeling data associated with the subject's body;

create a second composite visual feed from the received body modeling data and the video data received via at least the second camera; and display, via the display of the augmented reality-enabled device, the second composite visual feed.

5. The system of claim 1, wherein the one or more processors of the augmented reality-enabled device are further configured to:

detect, based on the video data received from at least the first camera, completion of a predetermined action associated with the medical device and/or the packaging of the medical device; and automatically switch from receiving video data via at least the first camera to receiving video data via at least the second camera.

6. The system of claim 5, wherein the predetermined action is indicative of the medical device leaving a first field of view of at least the first camera of the augmented reality-enable device.

7. The system of claim 6, wherein the predetermined action is indicative of the medical device entering a second field of view of at least the second camera of the augmented reality-enabled device.

8. The system of claim 1, wherein the one or more processors of the augmented reality-enable device are further configured to:

track, using the video data received via at least the first camera, a relative position and/or orientation of the medical device and/or the packaging of the medical device; and create a first composite visual feed from the three-dimensional model data and the video data received via at least the first camera, wherein the first composite visual feed is a dynamic composite visual feed that updates a relative position and/or orientation of the three-dimensional model data based on the tracking of the relative position and/or orientation of the medical device and/or the packaging of the medical device.

9. The system of claim 4, wherein the one or more processors of the augmented reality-enabled device are further configured to:

track, using the video data received via at least the second camera, a relative position and/orientation of the subject's body; and create a second composite visual feed from the body modeling data and the video data received via at least the second camera, wherein the second composite visual feed is a dynamic composite visual feed that updates a relative position and/or orientation of the body modeling data based on the tracking of the relative position and/or orientation of the subject's body.

10. The system of claim 1, wherein the one or more processors of the augmented reality-enabled device are further configured to:

identify, based on the video data received via at least the first camera, a type of the medical device and/or a packaging status of the medical device.

11. An augmented-reality system configured to assist a subject in the outpatient usage of a medical device, the system comprising:

a medical device configured to be coupled to a subject, the medical device comprising at least one physiological sensor configured to measure at least one physiological parameter associated with the subject when the medical device is coupled to the subject; and an augmented reality-enabled device comprising a display, at least a first camera having a first field of view, at least a second camera having a second field of view, a wireless communication device, and one or more processors in communication with the display, the wireless communication device, and the first and second cameras, wherein the one or more processors are configured to:

receive, via at least the first camera, video data comprising images of the medical device and/or a packaging of the medical device;

communicate, via the wireless communication device, with a remote content server to transmit the images of the medical device and/or the packaging of the medical device and to receive setup information associated with the medical device, wherein the setup information comprises three-dimensional model data associated with the medical device and/or the packaging of the medical device;

create a first composite visual feed from three-dimensional model data and the video data received via the first camera;

display, via the display of the augmented reality-enabled device, the first composite visual feed;

receive, via at least the second camera, video data comprising images of at least a portion of the subject's body;

communicate, via the wireless communication device, with the remote content server to transmit the images of the portion of the subject's body and receive body modeling data associated with the subject's body;

create a second composite visual feed from the received body modeling data and the video data received via at least the second camera; and display, via the display of the augmented reality-en-
abled device, the second composite visual feed.

12. A method of using an augmented-reality environment
to assist a subject in the usage of a medical device, the
method comprising:

receiving, via at least a first camera of an augmented
reality-enabled device, video data comprising images
of the medical device and/or a packaging of the medical
device;

transmitting, via a wireless communication device of the
augmented reality-enabled device, the images of the
medical device and/or a packaging of the medical
device;

receiving, via the wireless communication device of the
augmented reality-enabled device, setup information
associated with the medical device, wherein the setup
information comprises three-dimensional model data
associated with the medical device and/or the packag-
ing of the medical device;

creating, via one or more processors of the augmented
reality-enabled device, a first composite visual feed
from the three-dimensional model data and the video
data received via at least the first camera;

displaying, via a display of the augmented reality-enabled
device, the first composite visual feed.

13. The method of claim 12, further comprising:

receiving, via at least a second camera of the augmented
reality-enabled device, video data comprising images
of at least a portion of the subject's body;

transmitting, via the wireless communication device, the
images of at least the portion of the subject's body to
the remote content server;

receiving, via the wireless communication device, body
modeling data associated with the subject's body from
the remote content server;

creating, via the one or more processors of the augmented
reality-enabled device, a second composite visual feed
from the received body modeling data and the video
data received via at least the second camera; and displaying, via the display of the augmented reality-
enabled device, the second composite visual feed.

14. The method of claim 13, further comprising:

detecting, based on the video data received from at least
the first camera, completion of a predetermined action
associated with the medical device and/or the packag-
ing of the medical device; and automatically switching from receiving video data via at
least the first camera to receiving video data via at least
the second camera;

wherein at least the first camera has a first field of view,
and wherein at least the second camera has a second
field of view that is different than the first field of view.

15. The method of claim 13, further comprising:

tracking, via at least the first camera of the augmented
reality-enabled device, a relative position and/or orien-
tation of the medical device and/or the packaging of the
medical device;

creating, via the one or more processors of the augmented
reality-enabled device, a first composite visual feed
from the three-dimensional model data and the video
data received via at least the first camera, wherein the
first composite visual feed is a dynamic composite
visual feed that updates a relative position and/or
orientation of the three-dimensional model data based
on the tracking of the relative position and/or orienta-
tion of the medical device and/or the packaging of the
medical device;

tracking, via at least the second camera of the augmented
reality-enabled device, a relative position and/or orien-
tation of the subject's body; and creating, via the one or more processors of the augmented
reality-enabled device, a second composite visual feed
from the body modeling data and the video data
received via at least the second camera, wherein the
second composite visual feed is a dynamic composite
visual feed that updates a relative position and/or
orientation of the body modeling data based on the
tracking of the relative position and/or orientation of
the subject's body.

* * * * *